United States Patent
Yoshikawa et al.

(10) Patent No.: US 11,160,494 B2
(45) Date of Patent: Nov. 2, 2021

(54) RISK VALUE CALCULATION SYSTEM, RISK FACTOR PARAMETER CORRECTION SYSTEM, INFORMATION PROCESSING APPARATUS, RISK VALUE CALCULATION METHOD, RISK FACTOR PARAMETER CORRECTION METHOD, AND PROGRAM

(71) Applicant: Mitsubishi Electric Corporation, Tokyo (JP)

(72) Inventors: Tomoya Yoshikawa, Tokyo (JP); Hideto Kinjo, Tokyo (JP); Hiroo Kanamaru, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 17/279,591

(22) PCT Filed: Nov. 14, 2018

(86) PCT No.: PCT/JP2018/042068
§ 371 (c)(1),
(2) Date: Mar. 25, 2021

(87) PCT Pub. No.: WO2020/100223
PCT Pub. Date: May 22, 2020

(65) Prior Publication Data
US 2021/0307678 A1 Oct. 7, 2021

(51) Int. Cl.
*A61B 5/00* (2006.01)
*A61B 5/0205* (2006.01)
(Continued)

(52) U.S. Cl.
CPC ........ *A61B 5/4561* (2013.01); *A61B 5/02055* (2013.01); *B25J 9/1676* (2013.01); *G05B 19/0428* (2013.01); *A61B 2503/22* (2013.01)

(58) Field of Classification Search
CPC .............. A61B 5/4561; A61B 5/02055; A61B 2503/22; G05B 19/0428; B25J 9/1676
See application file for complete search history.

(56) References Cited

U.S. PATENT DOCUMENTS

| 2010/0087955 | A1 | 4/2010 | Tsusaka et al. |
| 2015/0006240 | A1* | 1/2015 | Kanamaru ............. F16P 3/147 |
| | | | 705/7.28 |
| 2017/0197313 | A1* | 7/2017 | Nishino ............ A61B 5/02055 |

FOREIGN PATENT DOCUMENTS

| JP | 61-42059 A | 2/1986 |
| JP | 2016-198839 A | 12/2016 |

(Continued)

OTHER PUBLICATIONS

International Search Report and Written Opinion dated Feb. 12, 2019, received for PCT Application PCT/JP2018/042068, Filed on Nov. 14, 2018, 8 pages including English Translation.

(Continued)

*Primary Examiner* — James J Yang
(74) *Attorney, Agent, or Firm* — Xsensus LLP

(57) ABSTRACT

A physical data acquirer included in an operator device acquires at least one of health data indicating a health condition of an operator or posture data indicating a posture of the operator. A distance determiner included in an information processing apparatus determines whether a distance between the operator and a machine is below a predetermined threshold. A corrector corrects an avoidability definition value defined as a value indicating a possibility of the operator avoiding a hazard caused by the machine in accordance with at least one of the health condition of the operator indicated by the health data acquired from the operator device or the posture of the operator indicated by the posture data acquired from the operator device. A risk value calculator calculates a risk value by substituting the corrected (Continued)

avoidability definition value and a riskiness definition value into a calculation function for the risk value.

12 Claims, 14 Drawing Sheets

(51) Int. Cl.
*B25J 9/16* (2006.01)
*G05B 19/042* (2006.01)

(56) References Cited

FOREIGN PATENT DOCUMENTS

| JP | 2017-100207 A | | 6/2017 | | |
|---|---|---|---|---|---|
| JP | 2017100207 A | * | 6/2017 | ............ | B25J 9/1676 |
| WO | 2009/001550 A1 | | 12/2008 | | |
| WO | 2013/105264 A1 | | 7/2013 | | |
| WO | WO-2013105264 A1 | * | 7/2013 | ............ | B25J 9/1676 |

OTHER PUBLICATIONS

Notice of Reasons for Refusal dated Jul. 2, 2019, received for JP Application 2019-530112, 4 pages including English Translation.
Decision to Grant dated Oct. 29, 2019, received for JP Application 2019-530112, 5 pages including English Translation.

\* cited by examiner

FIG. 4A

HEALTH DATA

| OPERATOR ID | 1001 |
|---|---|
| BODY TEMPERATURE (°C) | 36.5 |
| BLOOD PRESSURE (mmHg) | 69 |
| HEART RATE (bpm) | 70 |

FIG. 4B

POSTURE DATA

| OPERATOR ID | 1001 |
|---|---|
| ACCELERATION (m/s$^2$) | 1 |
| BENT-OVER ANGLE (kΩ) | 15 |

FIG. 4C

ATTRIBUTE DATA

| OPERATOR ID | 1001 |
|---|---|
| AGE (YEARS) | 35 |
| PERFORMANCE | 82 |

FIG. 4D

DISTANCE DATA

| MACHINE ID | OPERATOR ID | DISTANCE (m) |
|---|---|---|
| 0002 | 1003 | 1.5 m |
| | 1001 | 3 m |
| | 1004 | 4 m |
| | 1002 | 6 m |

RISK DEFINITION VALUE STORAGE

| MACHINE | MACHINE ID | HAZARD OCCURRENCE PROBABILITY | | | RISKINESS |
|---|---|---|---|---|---|
| | | AVOIDANCE POSSIBILITY | HAZARDOUS EVENT OCCURRENCE PROBABILITY | FREQUENCY OF ACCESSING HAZARD SOURCE | |
| PRESS MACHINE | 0001 | 5 | 7 | 6 | 8 |
| LATHE | 0002 | 5 | 9 | 4 | 6 |
| MILLING MACHINE | 0003 | 4 | 8 | 3 | 6 |
| DRILLING MACHINE | 0004 | 4 | 8 | 3 | 6 |

FIG. 6A

CORRECTION TABLE BASED ON BODY TEMPERATURE  360a

| BODY TEMPERATURE a (°C) | 0<=a<35.5 | 35.5<=a<37.0 | 37.0<=a<37.9 | 38.0<=a |
|---|---|---|---|---|
| CORRECTION CONSTANT | 2 | 0 | 1 | 2 |

FIG. 6B

CORRECTION TABLE BASED ON BLOOD PRESSURE  360b

| BLOOD PRESSURE b (mmHg) | 0<=b<50 | 50<=b<60 | 60<=b<80 | 80<=b<90 | 90<=b |
|---|---|---|---|---|---|
| CORRECTION CONSTANT | 4 | 3 | 0 | 3 | 4 |

FIG. 6C

CORRECTION TABLE BASED ON HEART RATE  360c

| HEART RATE c (bpm) | 0<=c<50 | 50<=c<60 | 60<=c<90 | 90<=c<100 | 100<=c |
|---|---|---|---|---|---|
| CORRECTION CONSTANT | 4 | 3 | 0 | 3 | 4 |

FIG. 7A

CORRECTION TABLE BASED ON ACCELERATION    360d

| ACCELERATION d (m/s$^2$) | 0<=d<3 | 3<=d<6 | 6<=d |
|---|---|---|---|
| CORRECTION CONSTANT | 0 | 1 | 2 |

FIG. 7B

CORRECTION TABLE BASED ON BENT-OVER ANGLE    360e

| BENT-OVER ANGLE e (kΩ) | 0<=e<30 | 30<=e<60 | 60<=e |
|---|---|---|---|
| CORRECTION CONSTANT | 0 | 1 | 2 |

FIG. 8A

CORRECTION TABLE BASED ON AGE                          360f

| AGE f (YEARS)        | 15<=f<40 | 40<=f<60 | 60<=f |
|----------------------|----------|----------|-------|
| CORRECTION CONSTANT  | 0        | 1        | 4     |

FIG. 8B

CORRECTION TABLE BASED ON PERFORMANCE                  360g

| PERFORMANCE g        | 0<=g<30 | 30<=g<70 | 70<=g |
|----------------------|---------|----------|-------|
| CORRECTION CONSTANT  | 2       | 1        | 0     |

RISK VALUE CALCULATION SYSTEM, RISK FACTOR PARAMETER CORRECTION SYSTEM, INFORMATION PROCESSING APPARATUS, RISK VALUE CALCULATION METHOD, RISK FACTOR PARAMETER CORRECTION METHOD, AND PROGRAM

CROSS-REFERENCE TO RELATED APPLICATION

The present application is based on PCT filing PCT/JP2018/042068, filed Nov. 14, 2018, the entire contents of which are incorporated herein by reference.

TECHNICAL FIELD

The present disclosure relates to a risk value calculation system, a risk factor parameter correction system, an information processing apparatus, a risk value calculation method, a risk factor parameter correction method, and a program.

BACKGROUND ART

To reduce risks of operators working around machines, various types of risk assessment have been discussed. For example, ISO 12100 defines estimation of the risk level based on the degree of a hazard caused by a machine, probability of hazardous events, exposure of people to hazard sources, and hazard avoidance possibility.

As an example of a method for estimating the risk level, Patent Literature 1 describes determination of a parameter indicating hazard avoidance possibility among risk factors used for risk estimation in accordance with the distance between an operator and a machine calculated from image data. Patent Literature 1 also describes calculation of a risk value indicating the risk level based on a parameter indicating hazard avoidance possibility determined in accordance with the distance between the operator and the machine, a parameter indicating exposure of the operator to the machine determined in accordance with the operation mode of the machine, and a parameter indicating the degree of a hazard caused by the machine.

The method described in Patent Literature 1 determines the parameter indicating hazard avoidance possibility in accordance with the distance between the operator and the machine. However, the possibility of the operator avoiding a hazard may differ between when the operator has good physical conditions and poor physical conditions. Patent Literature 2 describes a method for calculating a risk value based on the physical conditions and posture of an operator. Patent Literature 2 describes a robot that operates in cooperation with an operator. The robot measures the body temperature, blood pressure, and heart rate of the operator to acquire physical condition information, detects the posture of the operator to acquire posture information, and calculates a risk value based on the physical condition information and the posture information of the operator.

CITATION LIST

Patent Literature

Patent Literature 1: International Publication No. WO 2013/105264

Patent Literature 2: International Publication No. WO 2009/001550

SUMMARY OF INVENTION

Technical Problem

To acquire physical condition information of the operator, the robot with the structure described in Patent Literature 2 is to be in contact with the operator via an object to be carried. Thus, when spaced apart from the operator, the robot cannot acquire physical condition information and posture information of the operator. The structure described in Patent Literature 1 simply uniformly calculates the risk value in accordance with the distance between the operator and the machine, and cannot acquire a risk value based on the physical conditions of the operator.

An objective of the present disclosure is to enable acquisition of a risk value based on physical conditions of an operator who may be spaced apart from a machine.

Solution to Problem

To achieve the above objective, a risk value calculation system according to an aspect of the present disclosure includes an operator device wearable by an operator, and an information processing apparatus to calculate a risk value indicating a level of risk. Physical data acquisition means included in the operator device acquires at least one of health data indicating a health condition of the operator or posture data indicating a posture of the operator. Distance determination means included in the information processing apparatus determines whether a distance between the operator and a machine is below a predetermined threshold. Correction means included in the information processing apparatus corrects, in response to the distance determination means determining that the distance is below the threshold, an avoidability definition value defined as a value indicating a possibility of the operator avoiding a hazard caused by the machine in accordance with at least one of the health condition of the operator indicated by the health data acquired from the operator device or the posture of the operator indicated by the posture data acquired from the operator device. Risk value calculation means included in the information processing apparatus calculates the risk value by substituting the avoidability definition value corrected by the correction means and a riskiness definition value defined as a value indicating a degree of a hazard caused by the machine into a calculation function indicating a relationship between the avoidability definition value, the riskiness definition value, and the risk value.

Advantageous Effects of Invention

In the risk value calculation system according to the above aspect of the present disclosure, the operator device wearable by an operator acquires at least one of health data indicating a health condition of the operator or posture data indicating a posture of the operator. When determining that a distance between the operator and the machine is below a predetermined threshold, the information processing apparatus corrects an avoidability definition value defined as a value indicating a possibility of the operator avoiding a hazard caused by the machine in accordance with at least one of the health condition of the operator indicated by the health data acquired from the operator device or the posture of the operator indicated by the posture data acquired from the operator device. The information processing apparatus also calculates a risk value with the corrected avoidability definition value. This structure can acquire a risk value based on physical conditions of the operator who may be spaced apart from the machine.

BRIEF DESCRIPTION OF DRAWINGS

FIG. 4A is a table of example health data according to the embodiment;

FIG. 4B is a table of example posture data according to the embodiment;

FIG. 4C is a table of example attribute data according to the embodiment;

FIG. 4D is a table of example distance data according to the embodiment;

FIG. 5 is a table of example data stored in a risk definition value storage according to the embodiment;

FIG. 6A is an example correction table storing data based on body temperature according to the embodiment;

FIG. 6B is an example correction table storing data based on blood pressure according to the embodiment;

FIG. 6C is an example correction table storing data based on heart rate according to the embodiment;

FIG. 7A is an example correction table storing data based on acceleration according to the embodiment;

FIG. 7B is an example correction table storing data based on a bent-over angle according to the embodiment;

FIG. 8A is an example correction table storing data based on age according to the embodiment;

FIG. 8B is an example correction table storing data based on performance according to the embodiment;

DESCRIPTION OF EMBODIMENTS

Embodiment

A risk value calculation system according to an embodiment of the present disclosure will now be described in detail with reference to the drawings.

Figure 2:
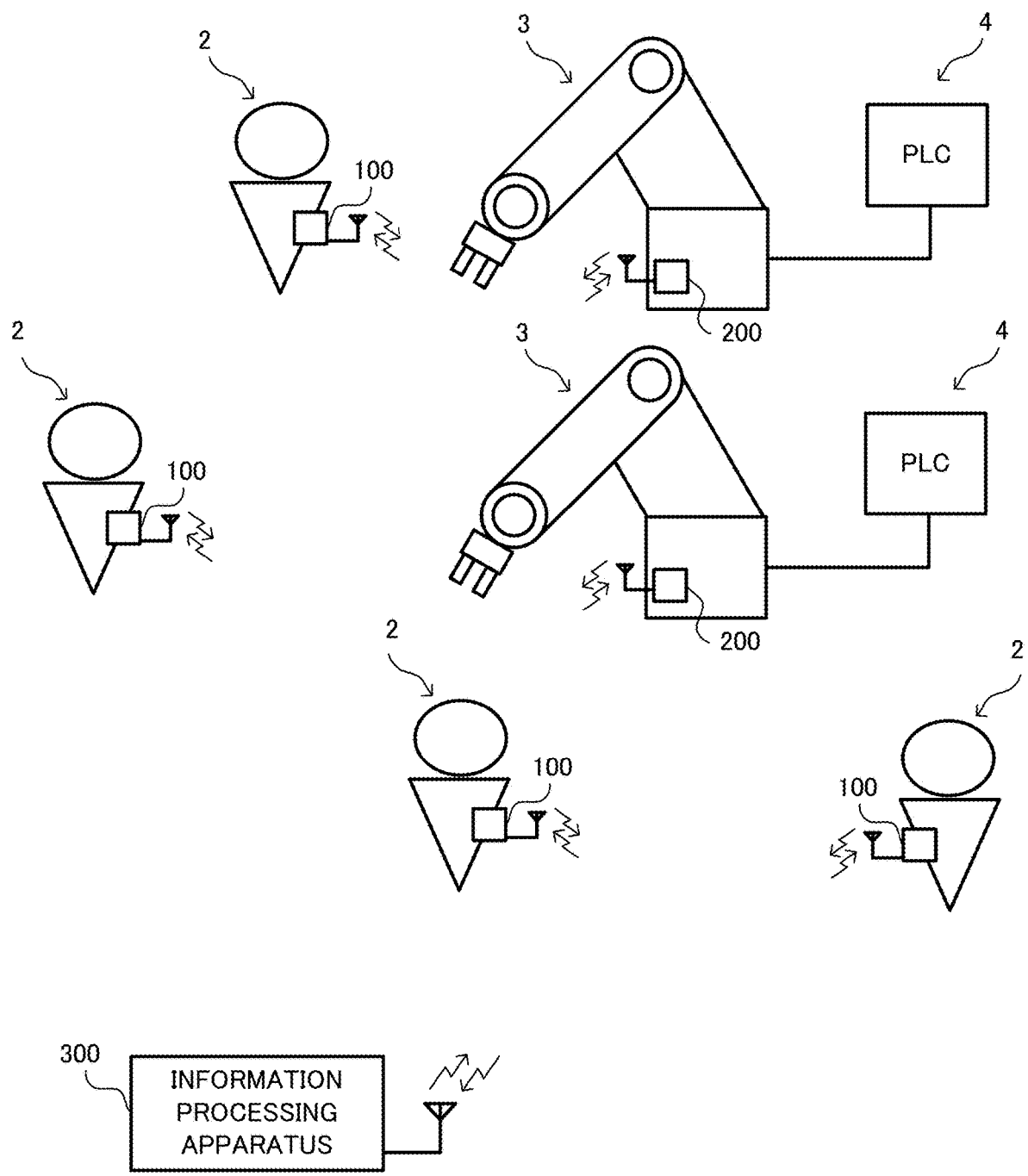
FIG. 2 is a schematic diagram of the risk value calculation system according to the embodiment.

A risk value calculation system 1 shown in FIG. 2 calculates risk values indicating the level of risk caused by machines 3 against operators 2. A risk value calculated by the risk value calculation system 1 is an estimate value of the level of a possible risk. In the example described below, a risk is a possibility of undesired occurrence. For example, a risk is a hazard to the operators 2 resulting from a hazardous event caused by the machines 3. The machines 3 are, for example, machine tools installed in a factory, and controlled by programmable logic controllers (PLCs) 4.

ISO 12100 defines calculation of a risk value with a function of the degree of a hazard caused by a hazard source and hazard occurrence probability. A function to calculate a risk value may be multiplication. For example, a risk value is calculated with Formula 1:

(degree of hazard caused by hazard source)×(hazard occurrence probability)  Formula (1)

The hazard occurrence probability in Formula (1) includes values indicating three factors, or specifically, (a) hazard avoidance possibility, (b) probability of hazardous events, and (c) exposure of people to a hazard source. The embodiment describes an example of a risk value calculated for each machine 3 serving as a hazard source with Formula (1).

In the example described below, the degree of a hazard caused by the machine 3 is estimated based on the degree of health impairment suffered by the operator 2 from the machine 3 and the range of a hazard. The range of a hazard depends on, for example, the number of operators 2 that suffer a hazard from the machine 3. The degree of the hazard will be described as riskiness below.

The value indicating (a) hazard avoidance possibility indicates the possibility of the operator 2 avoiding a hazard caused by the machine 3. The value indicating (b) probability of hazardous events indicates the probability of the machine 3 causing an event hazardous to the operator 2. The value indicating (c) exposure of people to a hazard source is estimated based on the time for which and the frequency at which the operator 2 is exposed to a hazardous condition. The hazard avoidance possibility may be hereafter referred to as avoidability below. The exposure of people to a hazard source may be hereafter referred to as the frequency of people accessing a hazard source. The probability of hazardous events may be hereafter referred to as the hazardous event occurrence probability.

Among the three factors of the hazard occurrence probability, the risk value calculation system 1 corrects a value of avoidability predetermined for each machine 3 in accordance with the physical conditions of each operator 2 and the attributes of each operator 2. The physical conditions of the operator 2 include the health condition and the posture of the operator 2.

For example, the operator 2 having good physical conditions may avoid a hazardous event. However, when the operator 2 has poor physical conditions, the operator 2 may lack, for example, reflexes or agility and cannot avoid the hazard. Thus, the health condition of the operator 2 is reflected in calculating a risk value. In addition, depending on the posture of the operator 2, the operator 2 cannot promptly avoid a hazard. Thus, the posture of the operator 2 is reflected in calculating the risk value. Depending on the attributes of the operator 2 including the age and performance, the operator 2 may be able or unable to promptly and appropriately avoid a hazard at a hazardous event. Thus, the attributes of the operator 2 are also reflected in calculating the risk value. In addition, the risk value calculation system 1 calculates the risk value with a corrected value of avoidability.

The structure of the risk value calculation system 1 will now be described. The risk value calculation system 1 shown in FIG. 1 includes an operator device 100 wearable by the operator 2, a machine-mounted device 200 mounted on the machine 3, and an information processing apparatus 300 that calculates a risk value based on information collected from the operator device 100 and the machine-mounted device 200. The operator device 100, the machine-mounted device 200, and the information processing apparatus 300 can wirelessly communicate with one another. As shown in FIG. 2, the operator device 100 is worn by each operator 2, and the machine-mounted device 200 is mounted on each machine 3.

Figure 3:
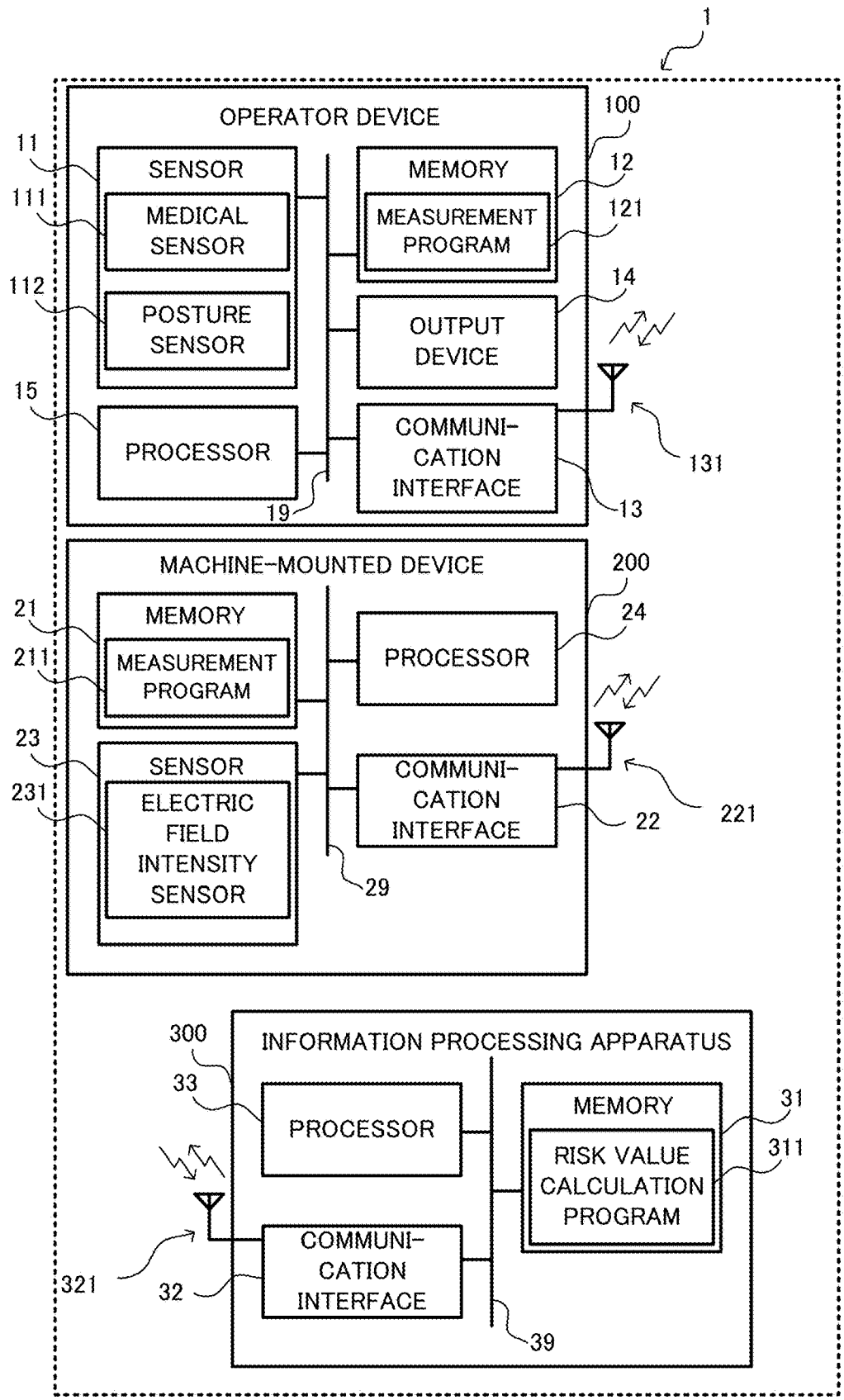
FIG. 3 is a block diagram of the risk value calculation system showing the hardware configuration according to the embodiment.

The operator device 100 acquires health data indicating the health condition of the operator 2 and posture data indicating the posture of the operator 2. The health data and the posture data will be described in detail later. The operator device 100 includes, for example, a wrist-watch wearable device and a sensor. As shown in FIG. 3, the operator device 100 includes, as hardware components, a sensor 11 that performs measurements relating to the health and posture of the operator 2, a memory 12 that stores various programs and data, a communication interface 13 that wirelessly communicates with the machine-mounted device 200 and the information processing apparatus 300, an output device 14 that outputs a sound, and a processor 15 that centrally controls the operator device 100. The sensor 11, the memory 12, and the communication interface 13 are connected to the processor 15 with a bus 19. The sensor 11, the memory 12, and the communication interface 13 communicate with the processor 15.

The sensor 11 includes a medical sensor 111 and a posture sensor 112. The medical sensor 111 includes a body temperature sensor that measures the body temperature of the operator 2, a blood pressure sensor that measures the blood pressure of the operator 2, and a heart rate sensor that measures the heart rate of the operator 2. The posture sensor 112 includes an acceleration sensor that measures the acceleration of the operator 2 and a curvature sensor that measures the bent-over angle of the operator 2. As controlled by the processor 15, the sensor 11 measures the body temperature, blood pressure, and heart rate of the operator 2, and outputs the measurement values to the processor 15. As controlled by the processor 15, the sensor 11 measures the acceleration and the bent-over angle of the operator 2, and outputs the measurement values to the processor 15.

The health data includes measurement values of the body temperature, blood pressure, and heart rate of the operator 2 measured by the medical sensor 111, the measured date and time, and an operator identification (ID) serving as identification information for identifying the operator 2 wearing the operator device 100. The posture data includes the acceleration and the bent-over angle of the operator 2 measured by the posture sensor 112 in the sensor 11, the measured date and time, and the operator ID for identifying the operator 2. For example, measuring the acceleration of the operator 2 for a predetermined period enables detection of the actions of the operator 2, such as standing, crouching, walking, and running. The acceleration of the operator 2 can be used to detect the operator 2 stumbling or falling.

The memory 12 includes a volatile memory and a non-volatile memory. The memory 12 stores a measurement program 121 for the operator device 100 to acquire health data indicating the health condition of the operator 2 and posture data indicating the posture of the operator 2. The measurement program 121 causes the processor 15 (described later) to implement the function of acquiring the health data and posture data of the operator 2. The memory 12 is used as a work memory for the processor 15.

The communication interface 13 includes an antenna 131 and wirelessly communicates with other devices. As controlled by the processor 15, the communication interface 13 wirelessly communicates with the machine-mounted device 200 and the information processing apparatus 300. More specifically, the communication interface 13 converts data provided from the processor 15 to electric signals, and transmits the resultant electric signals through radio waves to the machine-mounted device 200 or the information processing apparatus 300. The communication interface 13 retrieves electric signals from the radio waves received from the machine-mounted device 200 or the information processing apparatus 300, and outputs data restored from the electric signals to the processor 15.

The output device 14 includes a speaker, and outputs a sound based on an audio signal provided from the processor 15 through the speaker.

The processor 15 includes a micro-processing unit (MPU), and executes various programs stored in the memory 12 to implement the various functions of the operator device 100. In the embodiment, the processor 15 executes the measurement program 121 stored in the memory 12 to acquire, with the sensor 11, the health data indicating the health condition of the operator 2 and the posture data indicating the posture of the operator 2. The processor 15 transmits the acquired health data and posture data to the information processing apparatus 300 via the communication interface 13.

Figure 1:
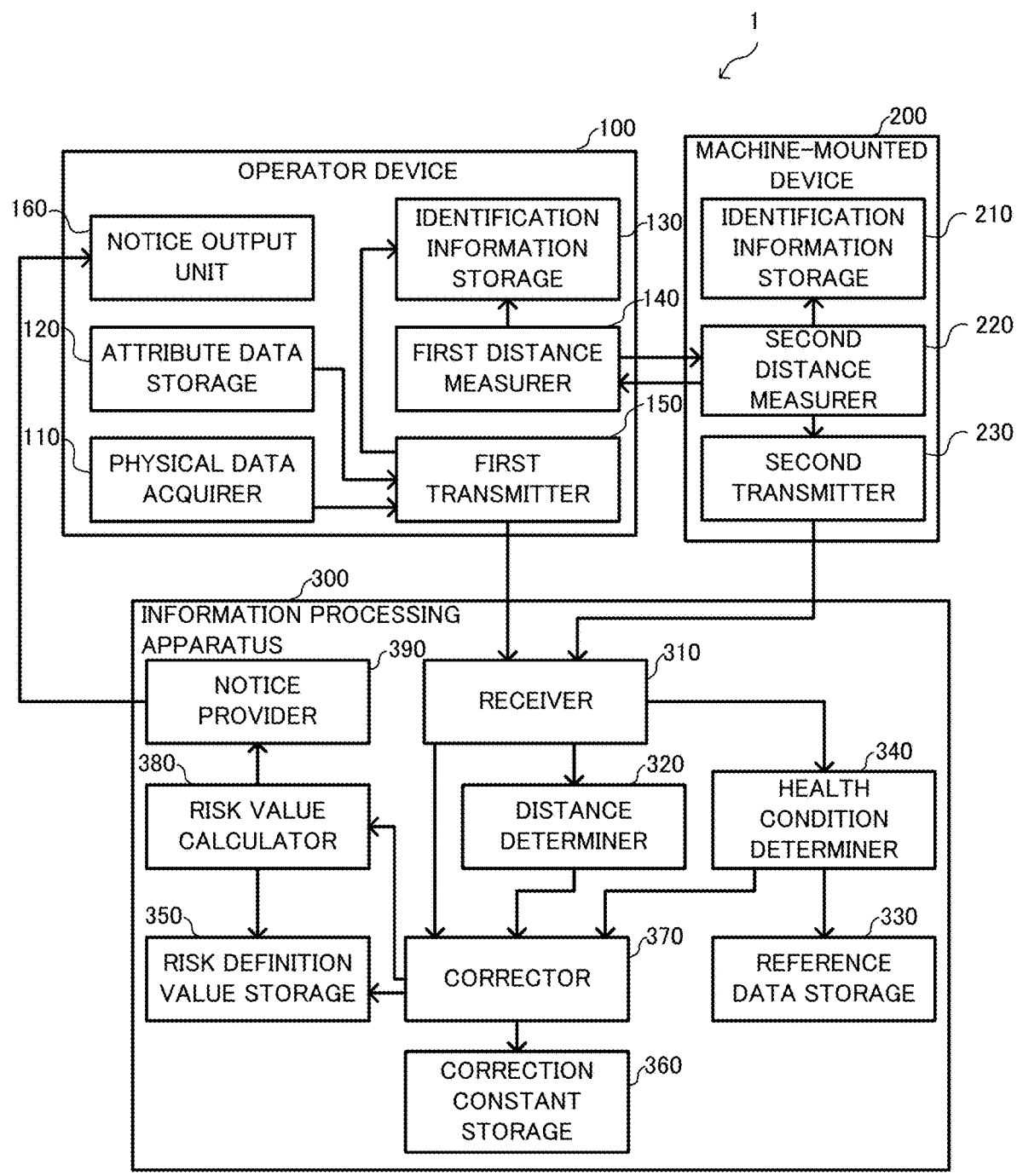
FIG. 1 is a functional block diagram of a risk value calculation system according to an embodiment of the present disclosure.

The machine-mounted device 200 shown in FIGS. 1 and 2 measures the distance between the operator device 100 and the machine-mounted device 200. As shown in FIG. 3, the machine-mounted device 200 includes, as hardware components, a memory 21 that stores various programs and data, a communication interface 22 that wirelessly communicates with the operator device 100 and the information processing apparatus 300, a sensor 23 including various sensors, and a processor 24 that centrally controls the machine-mounted device 200. The memory 21, the communication interface 22, and the sensor 23 are connected to the processor 24 with a bus 29. The memory 21, the communication interface 22, and the sensor 23 communicate with the processor 24.

The memory 21 includes a volatile memory and a non-volatile memory. The memory 21 stores a measurement program 211 to measure the distance between the operator device 100 and the machine-mounted device 200. The measurement program 211 causes the processor 24 (described later) to measure the distance between the operator device 100 and the machine-mounted device 200. The memory 21 is used as a work memory for the processor 24.

The communication interface 22 includes an antenna 221 and wirelessly communicates with other devices. As controlled by the processor 24, the communication interface 22 wirelessly communicates with the operator device 100 and the information processing apparatus 300. More specifically, the communication interface 22 converts data provided from the processor 24 to electric signals, and transmits the resultant electric signals, through radio waves, to the operator device 100 or the information processing apparatus 300. In addition, the communication interface 22 retrieves electric signals from the radio waves received from the operator device 100 or the information processing apparatus 300, and outputs data restored from the electric signals to the processor 24.

The sensor 23 includes an electric field intensity sensor 231 that measures electric field intensity. The sensor 23 measures the electric field intensity of the radio signals received by the machine-mounted device 200, and outputs the measurement value to the processor 24.

The processor 24 includes an MPU, and executes various programs stored in the memory 21 to implement the various functions of the machine-mounted device 200. In the embodiment, the processor 24 executes the measurement program 211 stored in the memory 21 to measure the distance between the operator device 100 and the machine-mounted device 200. The processor 24 transmits the measurement value of the distance to the information processing apparatus 300 via the communication interface 22.

The information processing apparatus 300 shown in FIGS. 1 and 2 calculates a risk value indicating the level of risk to the operator 2 based on data collected from the operator device 100 and the machine-mounted device 200.

As shown in FIG. 3, the information processing apparatus 300 includes, as hardware components, a memory 31 that stores various programs and data, a communication interface 32 that wirelessly communicates with the operator device 100 and the machine-mounted device 200, and a processor 33 that centrally controls the information processing apparatus 300. The memory 31 and the communication interface 32 are connected to the processor 33 with a bus 39. The memory 31 and the communication interface 32 communicate with the processor 33.

The memory 31 includes a volatile memory and a nonvolatile memory. The memory 31 stores a risk value calculation program 311 for calculating a risk value. The risk value calculation program 311 causes the processor 33 (described later) to calculate a risk value using data collected from the operator device 100 and the machine-mounted device 200. The memory 31 is used as a work memory for the processor 33.

The communication interface 32 includes an antenna 321 and wirelessly communicates with other devices. As controlled by the processor 33 (described later), the communication interface 32 wirelessly communicates with the operator device 100 and the machine-mounted device 200. More specifically, the communication interface 32 converts data provided from the processor 33 to electric signals, and transmits the resultant electric signals, through radio waves, to the operator device 100 or the machine-mounted device 200. In addition, the communication interface 32 retrieves electric signals from the radio waves received from the operator device 100 or the machine-mounted device 200, and outputs data restored from the electric signals to the processor 33.

The processor 33 includes an MPU and executes the risk value calculation program 311 stored in the memory 31 to calculate a risk value with the health data and posture data received from the operator device 100 via the communication interface 32 and the measurement value of the distance received from the machine-mounted device 200.

As shown in FIG. 1, the operator device 100 includes, as functional components, a physical data acquirer 110 that acquires health data and posture data of the operator 2, an attribute data storage 120 that stores attribute data of the operator 2, an identification information storage 130 that stores an operator ID for identifying the operator device 100, a first distance measurer 140 that measures the distance between the operator device 100 and the machine-mounted device 200, a first transmitter 150 that communicates with the information processing apparatus 300, and a notice output unit 160 that notifies a risk value provided from the information processing apparatus 300 to the operator 2.

The physical data acquirer 110 measures the body temperature, blood pressure, and heart rate of the operator 2, and provides health data including the operator ID and the measurement values shown in FIG. 4A to the first transmitter 150. In addition, the physical data acquirer 110 measures the acceleration and the bent-over angle of the operator 2, and provides posture data including the operator ID and the measurement values shown in FIG. 4B to the first transmitter 150. The functions of the physical data acquirer 110 are implemented by the medical sensor 111, the posture sensor 112, and the processor 15 shown in FIG. 3. The physical data acquirer 110 is an example of physical data acquisition means according to the present disclosure. Each of the measurement values of body temperature, blood pressure, and heart rate is an example of a healthcare measurement value according to the present disclosure. Each of the measurement values of acceleration and bent-over angle is an example of a posture measurement value according to the present disclosure. Each of body temperature, blood pressure, and heart rate is an example of a health factor according to the present disclosure. Each of acceleration and bent-over angle is an example of a posture factor according to the present disclosure.

The attribute data storage 120 shown in FIG. 1 stores attribute data that indicates attributes unique to the operator 2. As shown in FIG. 4C, attribute data includes the operator ID for identifying the operator 2, the age of the operator 2, and the value indicating the performance of the operator 2.

The attribute data includes age for the reason below. For example, whether the operator 2 can promptly avoid a hazard conceivably relates to the exercise capacity of the operator 2. Typically, the exercise capacity lowers with aging. The age of the operator 2 is thus reflected in calculation of the risk value.

The value indicating the performance of the operator 2 is a quantified value of the period of work experience of the operator 2. For example, when the operator 2 is fully experienced in the allocated work, the value indicating the performance of the operator 2 is large. When the operator 2 is inexperienced in the allocated work, the value indicating the performance of the operator 2 is small. In other words, a larger value indicating performance indicates that the operator is more fully experienced, and a smaller value indicating performance indicates that the operator is less experienced.

For example, when the operator 2 is an operator of the machine 3 as well as an expert fully experienced with the work for years, the operator 2 is regarded as being familiar with hazardous events that can occur in the machine 3. Thus, the operator 2 is expected to be highly capable of avoiding a hazard by, for example, promptly noticing or estimating an occurrence of a hazardous event. In contrast, when, for example, the operator 2 is a trainee operator of the machine 3, the operator 2 is less likely to highly capable of avoiding a hazard with a failure in, for example, promptly noticing or estimating an occurrence of a hazardous event. Thus, the performance of the operator 2 is reflected in calculation of the risk value. The functions of the attribute data storage 120 are implemented by the memory 12 shown in FIG. 3. The attribute data storage 120 is an example of attribute data storage means according to the present disclosure.

The identification information storage 130 shown in FIG. 1 stores the operator ID for identifying the operator device 100. In FIG. 2, multiple operators 2 each wear the operator device 100, and the risk value calculation system 1 includes multiple operator devices 100. The machine-mounted device 200 and the information processing apparatus 300 can uniquely identify each operator device 100 with the operator ID stored in the identification information storage 130. The functions of the identification information storage 130 are implemented by the memory 12 shown in FIG. 3.

The first distance measurer 140 shown in FIG. 1 measures the distance between the operator device 100 and the machine-mounted device 200 in cooperation with a second distance measurer 220 (described later) in the machine-mounted device 200. More specifically, in response to a distance measurement signal from the second distance measurer 220 included in the machine-mounted device 200, the first distance measurer 140 transmits the operator ID stored in the identification information storage 130 to the machine-mounted device 200 that has transmitted the distance measurement signal. The distance measurement signal is transmitted from the machine-mounted device 200 to request the operator ID. The distance measurement signal includes a command requesting the operator ID for distance measurement and a machine ID for identifying the machine-mounted device 200 that has transmitted the distance measurement signal. Thus, the first distance measurer 140 can specify the transmitter of the distance measurement signal.

As described in detail later, in the embodiment, the second distance measurer 220 included in the machine-mounted device 200 measures the distance between the operator device 100 and the machine-mounted device 200 based on the response signal received from the first distance measurer 140 and including the operator ID of the operator device 100. The functions of the first distance measurer 140 are implemented by the communication interface 13 and the processor 15 shown in FIG. 3. The first distance measurer 140 is an example of first distance measurement means according to the present disclosure.

The first transmitter 150 shown in FIG. 1 transmits the health data and posture data of the operator 2 provided from the physical data acquirer 110 and attribute data stored in the attribute data storage 120 to the information processing apparatus 300. The functions of the first transmitter 150 are implemented by the communication interface 13 and the processor 15 shown in FIG. 3. The first transmitter 150 is an example of first communication means according to the present disclosure.

The notice output unit 160 shown in FIG. 1 audibly outputs a message including a risk value notified by the information processing apparatus 300 and an alert to the operator 2 in accordance with the risk value. The functions of the notice output unit 160 are implemented by the communication interface 13, the output device 14, and the processor 15 shown in FIG. 3.

As shown in FIG. 1, the machine-mounted device 200 includes, as functional components, an identification information storage 210 that stores a machine ID for identifying the machine-mounted device 200, the second distance measurer 220 that measures the distance between the machine-mounted device 200 and the operator device 100, and a second transmitter 230 that communicates with the information processing apparatus 300.

The identification information storage 210 stores the machine ID for identifying the machine-mounted device 200. In FIG. 2, the machine-mounted device 200 is mounted on each machine 3. Thus, the risk value calculation system 1 includes multiple machine-mounted devices 200. The operator device 100 and the information processing apparatus 300 can uniquely identify each machine-mounted device 200 with the machine ID stored in the identification information storage 210. The functions of the identification information storage 210 are implemented by the memory 21 shown in FIG. 3.

The second distance measurer 220 shown in FIG. 1 measures the distance between the operator device 100 and the machine-mounted device 200 in cooperation with the first distance measurer 140 in the operator device 100. More specifically, the second distance measurer 220 broadcasts the distance measurement signals at predetermined intervals. In response to the distance measurement signal, the first distance measurer 140 in the operator device 100 transmits a response signal including the operator ID to the machine-mounted device 200. In response to the response signal including the operator ID of the operator device 100 from the operator device 100, the second distance measurer 220 calculates the distance to the operator device 100 based on the electric field intensity of the received response signal.

In the embodiment, the operator device 100 and the machine-mounted device 200 transmit radio signals with the same transmission power. The second distance measurer 220 calculates the distance between the operator device 100 that has transmitted a response signal and the machine-mounted device 200 that has received the response signal based on attenuation calculated from the difference in electric field intensity between the reception and the transmission of the response signal. As shown in FIG. 2, the operator device 100 is worn by each operator 2, and the machine-mounted device 200 is mounted on each machine 3. Thus, the distance calculated by the second distance measurer 220 is substantially equal to the distance between the operator 2 and the machine 3.

The second distance measurer 220 provides, to the second transmitter 230, distance data including the machine ID of the machine-mounted device 200, the operator ID of the operator device 100 that has transmitted the response signal, and the acquired distance between the operator device 100 and the machine-mounted device 200 as shown in FIG. 4D. The functions of the second distance measurer 220 are implemented by the communication interface 22, the electric field intensity sensor 231 in the sensor 23, and the processor 24 shown in FIG. 3. The second distance measurer 220 is an example of second distance measurement means according to the present disclosure.

The second transmitter 230 shown in FIG. 1 transmits distance data provided from the second distance measurer 220 to the information processing apparatus 300. The functions of the first transmitter 150 are implemented by the communication interface 22 and the processor 24 shown in FIG. 3. The second transmitter 230 is an example of second communication means according to the present disclosure.

As shown in FIG. 1, the information processing apparatus 300 includes, as functional components, a receiver 310, a distance determiner 320, a reference data storage 330, a health condition determiner 340, a risk definition value storage 350, a correction constant storage 360, a corrector 370, a risk value calculator 380, and a notice provider 390. The receiver 310 receives health data, posture data, and attribute data from the operator device 100 and distance data from the machine-mounted device 200. The distance determiner 320 determines the conditions of the distance between the operator 2 and the machine 3. The reference data storage 330 is used for determining the health condition. The health condition determiner 340 determines the health condition of the operator 2. The risk definition value storage 350 stores definition values of risk factors. The correction constant storage 360 stores constants used for correcting the definition values of the risk factors. The corrector 370 corrects the definition values of the risk factors. The risk value calculator 380 calculates a risk value. The notice provider 390 notifies a risk value to the operator device 100.

The receiver 310 receives health data, posture data, and attribute data from the operator device 100, and provides the received health data to the health condition determiner 340. The receiver 310 also provides the received health data, posture data, and attribute data to the corrector 370. The receiver 310 also receives distance data from the machine-mounted device 200, and provides the received distance to the distance determiner 320. The functions of the receiver 310 are implemented by the communication interface 32 and the processor 33 shown in FIG. 3.

The distance determiner 320 shown in FIG. 1 determines whether the distance between the operator device 100 identified with the operator ID and the machine-mounted device 200 identified with the machine ID is below a predetermined threshold based on the distance data provided from the receiver 310. In the embodiment, when the distance between the operator device 100 and the machine-mounted device 200 is below the predetermined threshold, the operator 2 is regarded as being adjacent to the machine 3. When the distance determiner 320 determines that the distance between the operator device 100 and the machine-mounted device 200 is below the predetermined threshold, the distance determiner 320 provides the operator ID of the operator device 100 and the machine ID of the machine-mounted device 200 to the corrector 370. The functions of the distance determiner 320 are implemented by the memory 31 and the processor 33 shown in FIG. 3. The distance determiner 320 is an example of distance determination means according to the present disclosure.

The reference data storage 330 shown in FIG. 1 stores data indicating a reference value of the health condition of the operator 2 for the health condition determiner 340 (described later) to determine whether the operator 2 has a normal health condition, and the operator ID of the operator 2. Data indicating the reference value includes a reference value of body temperature, a reference value of blood pressure, and a reference value of heart rate. The reference value of body temperature is a mean value of multiple measurement values of body temperature measured when the operator 2 is in good health. The reference value of blood pressure is a mean value of multiple measurement values of diastolic blood pressure measured when the operator 2 is in good health. The reference value of heart rate is a mean value of multiple measurement values of heart rate measured when the operator 2 is in good health. The functions of the reference data storage 330 are implemented by the memory 31 shown in FIG. 3.

The health condition determiner 340 shown in FIG. 1 determines whether the operator 2 has a normal health condition based on the health data of the operator 2 provided from the operator device 100 via the receiver 310 and reference data stored in the reference data storage 330, and provides the determination result to the corrector 370.

The health condition determiner 340 substitutes, into the formula below, the recent n measurement values of body temperature including the current measurement value of body temperature and the reference value of body temperature stored in the reference data storage 330 to calculate the standard deviation of measurement values of body temperature. For example, five recently acquired measurement values of body temperature are used for calculating the standard deviation. In the formula below, n denotes the number of measurement values, xi denotes the measurement value, and xm denotes the reference value of body temperature.

$$\sqrt{\frac{1}{n}\sum_{i=1}^{n}(x_i - x_m)^2}$$

The health condition determiner 340 determines that the operator 2 has an abnormal health condition when the calculated standard deviation of the measurement values of body temperature exceeds a predetermined threshold, serving as a criterion for body temperature.

Similarly, the health condition determiner 340 calculates the standard deviation of measurement values of blood pressure. The health condition determiner 340 determines that the operator 2 has an abnormal health condition when the calculated standard deviation of the measurement values of blood pressure exceeds a predetermined threshold, serving as a criterion for blood pressure.

Similarly, the health condition determiner 340 calculates the standard deviation of measurement values of heart rate. The health condition determiner 340 determines that the operator 2 has an abnormal health condition when the calculated standard deviation of measurement values of heart rate exceeds a predetermined threshold, serving as a criterion for heart rate.

When the health condition determiner 340 determines that the operator 2 has an abnormal health condition based on any of the measurement values of body temperature, blood pressure, and heart rate provided from the operator device 100, the health condition determiner 340 provides the result indicating that the operator 2 has an abnormal health condition to the corrector 370 together with the operator ID of the operator device 100. In contrast, when the health condition determiner 340 determines that the operator 2 has a normal health condition, the health condition determiner 340 provides the result indicating that the operator 2 has a normal health condition to the corrector 370 together with the operator ID of the operator device 100. The functions of the health condition determiner 340 are implemented by the processor 33 shown in FIG. 3. The health condition determiner 340 is an example of health condition determination means according to the present disclosure.

The risk definition value storage 350 shown in FIG. 1 stores definition values defined as risk factor parameters used for calculating risk values. The definition values of risk factors are defined for each machine 3. As shown in FIG. 5, the risk definition value storage 350 stores, for each machine 3, a definition value defined as a value indicating the possibility of the operator 2 avoiding a hazard (avoidability definition value), a definition value defined as a value indicating the probability of hazardous events caused by the machine 3 (a definition value for hazardous event occurrence probability), a definition value defined as a value indicating the frequency of the operator 2 accessing the machine 3 (a definition value for the frequency of accessing a hazard source), and a riskiness definition value. The risk definition value storage 350 is an example of risk definition value storage means according to the present disclosure.

Larger avoidability definition values indicate that the operator 2 can avoid a hazard less easily. Larger definition values for hazardous event occurrence probability indicate that the probability of hazardous events increases. Larger definition values for the frequency of accessing a hazard source indicate that the operator 2 is more likely to touch or approach the machine 3. The riskiness definition values indicate the degree of a hazard caused by the machine 3 and affecting the operator 2. The definition values stored in the risk definition value storage 350 are determined based on, for example, past statistic data. The functions of the risk definition value storage 350 are implemented by the memory 31 shown in FIG. 3.

The correction constant storage 360 shown in FIG. 1 stores correction constants used by the corrector 370 (described later) to correct the definition values indicating avoidability stored in the risk definition value storage 350 based on health data, posture data, and attribute data. As shown in FIGS. 6A to 6C, the correction constant storage 360 includes correction tables 360a, 360b, and 360c for storing correction constants defined for each measurement item of health data. As shown in FIGS. 7A and 7B, the correction constant storage 360 includes correction tables 360d and 360e for storing correction constants defined for each measurement item of posture data. As shown in FIGS. 8A and 8B, the correction constant storage 360 includes correction tables 360f and 360g for storing correction constants defined for each measurement item of attribute data. The functions of the correction constant storage 360 are implemented by the memory 31 shown in FIG. 3. The correction constant storage 360 is an example of correction constant storage means according to the present disclosure. Each of the correction constants defined for each measurement item of health data is an example of a first correction constant according to the present disclosure. Each of the correction constants defined for each measurement item of posture data is an example of a second correction constant according to the present disclosure. Each of the correction constants defined for each measurement item of attribute data is an example of a third correction constant according to the present disclosure.

The corrector 370 shown in FIG. 1 corrects, based on health data, posture data, and attribute data, the avoidability definition value stored in the risk definition value storage 350 for the machine 3 including the machine-mounted device 200 identified with the machine ID provided from the distance determiner 320. The corrector 370 provides the corrected avoidability definition value to the risk value calculator 380 together with the machine ID and the operator ID provided from the distance determiner 320. The functions of the corrector 370 are implemented by the processor 33 shown in FIG. 3. The corrector 370 is an example of correction means according to the present disclosure.

The processing performed by the corrector 370 will be described. First, when the health condition determiner 340 determines that the operator 2 has an abnormal health condition, the corrector 370 corrects the avoidability definition value defined for the relevant machine 3 in the risk definition value storage 350 with the correction constants shown in FIGS. 6A to 6C corresponding to the measurement values included in health data.

The corrector 370 also corrects the avoidability definition value defined for the relevant machine 3 in the risk definition value storage 350 with the correction constants shown in FIGS. 7A and 7B corresponding to the measurement values of posture data of the operator 2. The corrector 370 also corrects the avoidability definition value defined for the relevant machine 3 in the risk definition value storage 350 with the correction constants shown in FIGS. 8A and 8B corresponding to the attribute values included in the attribute data of the operator 2.

More specifically, when the health condition determiner 340 determines that the operator 2 has an abnormal health condition, the corrector 370 calculates a corrected avoidability definition value with Formula (2) below. Formula (2) is an example of a correction function according to the present disclosure.

Corrected avoidability definition value=avoidability definition value stored in risk definition value storage 350 for relevant machine 3+correction constant stored in correction table 360a shown in FIG. 6A corresponding to measurement value of body temperature of operator 2+correction constant stored in correction table 360b shown in FIG. 6B corresponding to measurement value of blood pressure of operator 2+correction constant stored in correction table 360c shown in FIG. 6C corresponding to measurement value of heart rate of operator 2+correction constant stored in correction table 360d shown in FIG. 7A corresponding to measurement value of acceleration of operator 2+correction constant stored in correction table 360e shown in FIG. 7B corresponding to measurement value of bent-over angle of operator 2+correction constant stored in correction table 360f shown in FIG. 8A corresponding to age of operator 2+correction constant stored in correction table 360g shown in FIG. 8B corresponding to value indicating performance of operator 2    Formula (2)

When the health condition determiner 340 determines that the operator 2 does not have an abnormal health condition, or in other words, has a normal health condition, the corrector 370 calculates a corrected avoidability definition value with Formula (3) below. Formula (3) is an example of a correction function according to the present disclosure.

Corrected avoidability definition value=avoidability definition value stored in risk definition value storage 350 for relevant machine 3+correction constant stored in correction table 360d shown in FIG. 7A corresponding to measurement value of acceleration of operator 2+correction constant stored in correction table 360e shown in FIG. 7B corresponding to measurement value of bent-over angle of operator 2+correction constant stored in correction table 360f shown in FIG. 8A corresponding to age of operator 2+correction constant stored in correction table 360g shown in FIG. 8B corresponding to value indicating performance of operator 2    Formula (3)

The risk value calculator 380 shown in FIG. 1 calculates a risk value with Formula (4) below for each combination of the operator device 100 identified with the operator ID and the machine-mounted device 200 identified with the machine ID provided from the corrector 370, based on the corrected avoidability definition value provided from the corrector 370, the value for hazardous event occurrence probability, the value of access frequency, and the value of riskiness defined in the risk definition value storage 350 shown in FIG. 5. Formula (4) is an example of a calculation function according to the present disclosure.

Risk value=(corrected avoidability definition value+ definition value for hazardous event occurrence probability stored in risk definition value storage 350+definition value for frequency of accessing hazard source stored in risk definition value storage 350)×riskiness stored in risk definition value storage 350    Formula (4)

The risk value calculator 380 provides the calculated risk value to the notice provider 390 together with the operator ID and the machine ID. The functions of the risk value calculator 380 are implemented by the processor 33 shown in FIG. 3. The risk value calculator 380 is an example of risk value calculation means according to the present disclosure.

The notice provider 390 shown in FIG. 1 notifies the risk value provided from the risk value calculator 380 to the corresponding operator device 100. The functions of the notice provider 390 are implemented by the communication interface 32 and the processor 33 shown in FIG. 3.

The process of calculating a risk value performed by the operator device 100, the machine-mounted device 200, and the information processing apparatus 300 in cooperation will now be described.

First, a measurement process in which the processor 15 in the operator device 100 shown in FIG. 3 executes the measurement program 121 to measure the health condition and the posture of the operator 2 will be described. To acquire health data and posture data, the processor 15 performs the measurement process of measuring the health condition and the posture of the operator 2 at preset intervals. In the measurement process described below, the operator device 100 also measures the distance between the operator device 100 and the machine-mounted device 200 in cooperation with the machine-mounted device 200.

Figure 9:
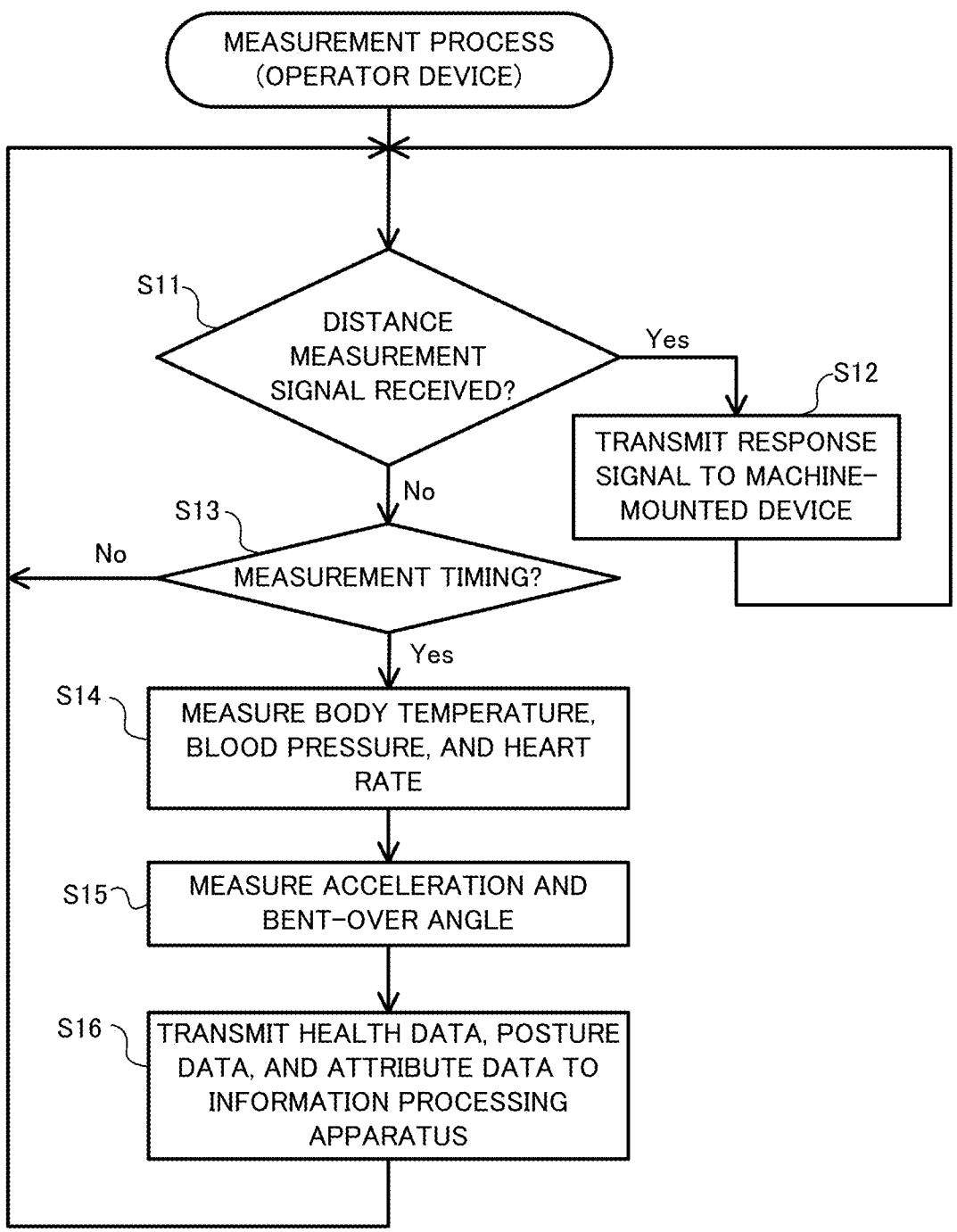
FIG. 9 is a flowchart showing a measurement process performed by an operator device according to the embodiment.

As shown in FIG. 9, the processor 15 determines whether the operator device 100 has received a distance measurement signal from the machine-mounted device 200 (step S11). When determining that the operator device 100 has received the distance measurement signal from the machine-mounted device 200 via the communication interface 13 (Yes in step S11), the processor 15 transmits a response signal including the operator ID of the operator device 100 to the machine-mounted device 200 identified with the machine ID included in the distance measurement signal via the communication interface 13 (step S12).

In contrast, when determining that the operator device 100 has not received the distance measurement signal from the machine-mounted device 200 (No in step S11), the processor 15 determines whether the timing for measuring the health condition and the posture of the operator 2 has come (step S13). For example, the processor 15 records the measurement date and time in the memory 12 every time the health condition and the posture are measured. When determining that a predetermined time has passed from the previous measurement, the processor 15 determines that the measurement timing has come.

When determining that the measurement timing has come (Yes in step S13), the processor 15 measures the body temperature, blood pressure, and heart rate of the operator 2 with the medical sensor 111 shown in FIG. 3 (step S14), and stores the measurement values in the memory 12. As shown in FIG. 9, the processor 15 then measures the acceleration and the bent-over angle of the operator 2 with the posture sensor 112 shown in FIG. 3 (step S15), and stores the measurement values in the memory 12.

The processor 15 transmits health data, posture data, and attribute data to the information processing apparatus 300 (step S16). More specifically, the processor 15 transmits, to the information processing apparatus 300 via the communication interface 13, health data shown in FIG. 4A including the operator ID and the measurement values of body temperature, blood pressure, and heart rate measured in step S14, posture data shown in FIG. 4B including the operator ID and the measurement values of acceleration and bent-over angle measured in step S15, and attribute data shown in FIG. 4C including the operator ID and the values indicating the age and performance of the operator 2.

As shown in FIG. 9, when determining in step 13 that the measurement timing has not come (No in step S13), the processor 15 performs the processing in step S11 again. This is the measurement process of the operator device 100.

A measurement process in which the processor 24 in the machine-mounted device 200 shown in FIG. 3 executes the measurement program 211 to measure the distance between the operator device 100 and the machine-mounted device 200 will now be described.

Figure 10:
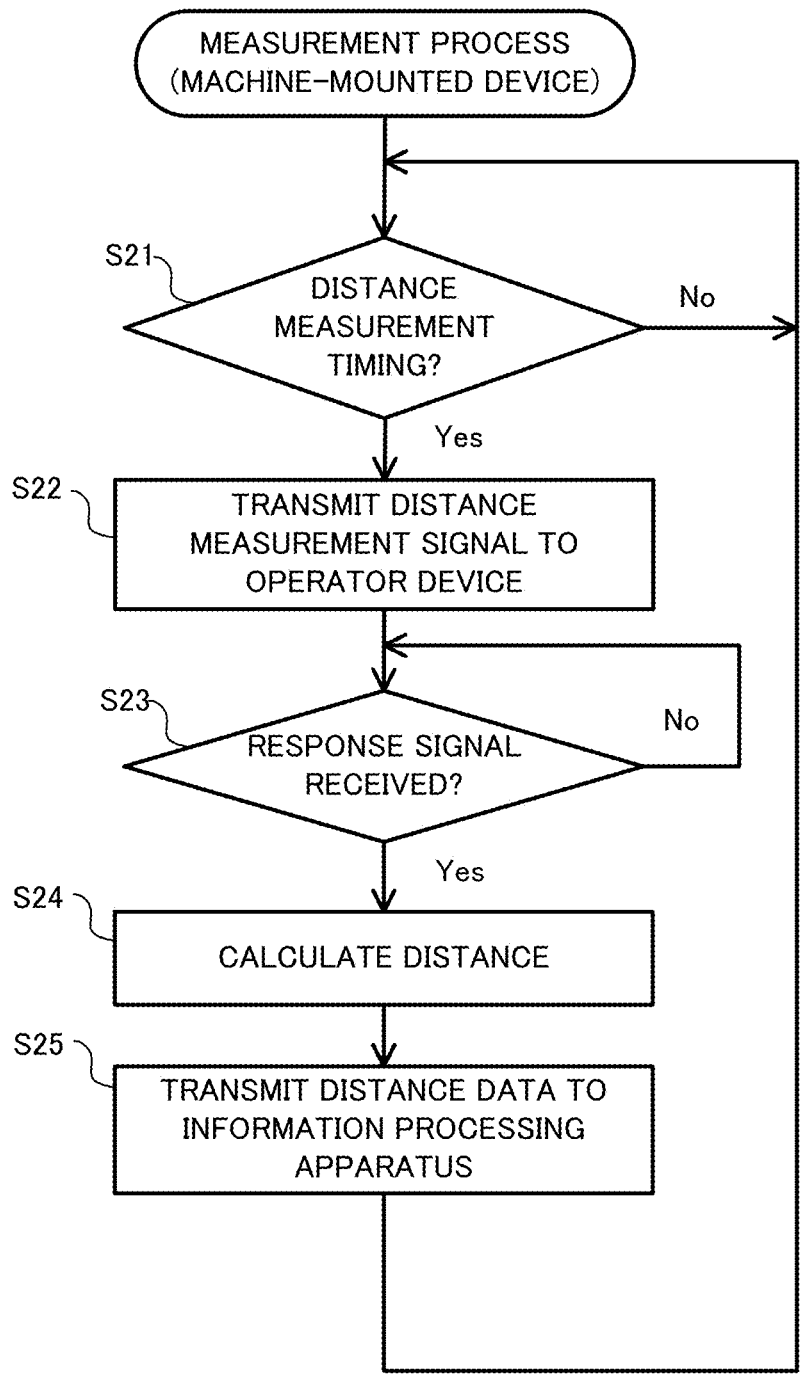
FIG. 10 is a flowchart showing a measurement process performed by a machine-mounted device according to the embodiment.

As shown in FIG. 10, the processor 24 determines whether the timing for measuring the distance has come (step S21). For example, the processor 24 records the transmission date and time in the memory 21 every time a distance measurement signal is transmitted. When determining that a predetermined time has passed, the processor 24 determines that the measurement timing has come.

When determining that the measurement timing has come (Yes in step S21), the processor 24 transmits the distance measurement signal to the operator device 100 via the communication interface 22 (step S22). The processor 24 broadcasts the distance measurement signal. The processor 24 then awaits until receiving a response signal including the operator ID of the operator device 100 from the operator device 100 via the communication interface 22 (No in step S23).

In response to the response signal from the operator device 100 (Yes in step S23), the processor 24 calculates the distance between the operator device 100 identified with the operator ID included in the response signal and the machine-mounted device 200 based on the electric field intensity of the received response signal (step S24). The processor 24 transmits, to the information processing apparatus 300 via the communication interface 22, distance data shown in FIG. 4D including the machine ID, the operator ID, and the calculated distance (step S25). This is the measurement process performed by the machine-mounted device 200.

The processing performed by the processor 33 in the information processing apparatus 300 shown in FIG. 3 to calculate a risk value based on health data, posture data, and attribute data provided from the operator device 100 and distance data provided from the machine-mounted device 200 will now be described.

First, the processor 33 calculates, as a preprocess, the standard deviations of the measurement values indicating the health condition from the health data of the operator 2. As described above, the operator device 100 transmits health data, posture data, and attribute data to the information processing apparatus 300 at preset intervals. The machine-mounted device 200 transmits distance data to the information processing apparatus 300 at preset intervals. Thus, the processor 33 performs the preprocess below at preset intervals.

Figure 11:
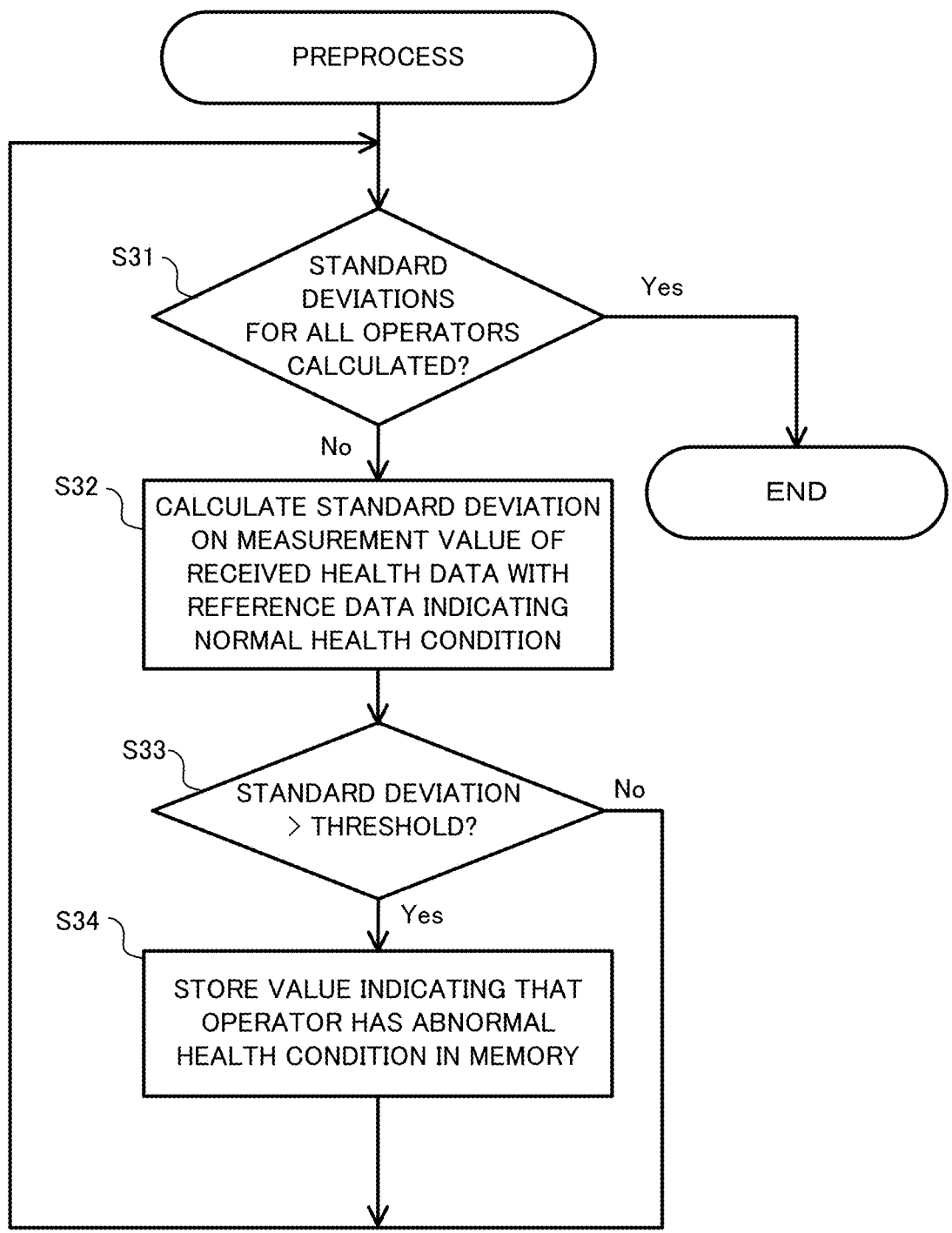
FIG. 11 is a flowchart showing a preprocess of risk value calculation performed by an information processing apparatus according to the embodiment.

As shown in FIG. 11, the processor 33 repeats the processing in step S32 and subsequent steps until the standard deviations of the measurement values indicating the health condition are calculated on all the pieces of health data received from each operator device 100, or in other words, for each operator 2 (No in step S31). For example, the processor 33 calculates the standard deviations of the measurement values indicating the health condition in ascending order of the operator IDs included in the health data.

In step S32, the processor 33 reads, from the memory 12, the reference data indicating the normal health condition of the operator 2 identified with the operator ID included in the health data, and calculates, for each measurement item, the standard deviation on the health data received from the operator device 100 with the reference data (step S32).

More specifically, the processor 33 calculates, as the standard deviation of body temperature, the square root of the difference between the reference value of the body temperature of the operator 2 included in the reference data and the measurement value of the body temperature of the operator 2 included in the health data received from the operator device 100. The processor 33 also similarly calculates the standard deviations of blood pressure and heart rate.

The processor 33 determines whether the standard deviations calculated in step S32 are larger than predetermined thresholds (step S33). More specifically, the processor 33 determines whether the calculated standard deviation of body temperature is larger than the threshold for the standard deviation of body temperature. The processor 33 determines whether the calculated standard deviation of blood pressure is larger than the threshold for the standard deviation of blood pressure. The processor 33 determines whether the calculated standard deviation of heart rate is larger than the threshold for the standard deviation of heart rate.

When determining that the standard deviation of any of body temperature, blood pressure, and heart rate calculated in step S32 is larger than the threshold (Yes in step S33), the processor 33 stores the value indicating that the operator 2 has an abnormal health condition in the memory 31 together with the operator ID of the operator device 100 (step S34). The processor 33 then performs the processing in step S31 and subsequent steps again, and repeats determining whether all the pieces of health data received from each operator device 100, or in other words, each operator 2 has a normal or abnormal health condition. When the processor 33 ends calculating the standard deviations of measurement values for all the pieces of health data received from each operator device 100 (Yes in step S31), the processor 33 ends the preprocess.

After performing the preprocess on all the pieces of health data received from each operator device 100, the processor 33 performs a risk value calculation process for calculating a risk value for each operator 2. The example below uses an example system including N machine-mounted devices 200.

Figure 12:
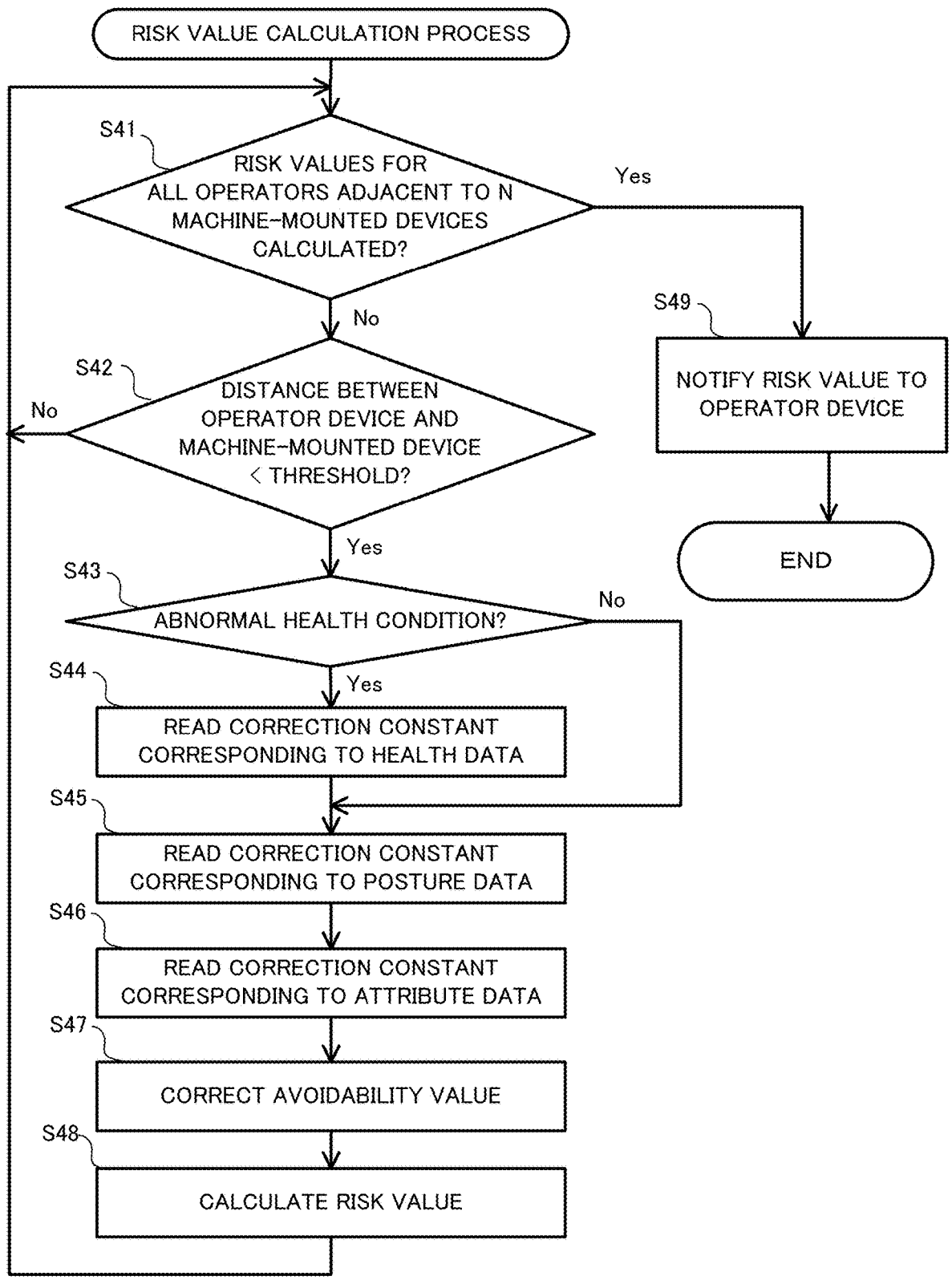
FIG. 12 is a flowchart showing a risk value calculation process performed by the information processing apparatus according to the embodiment.

As shown in FIG. 12, the processor 33 performs the processing in step S42 and subsequent steps until the processor 33 ends calculating risk values for all the operators 2 adjacent to the N machine-mounted devices 200 (No in step S41).

The processor 33 determines whether the distance between the operator device 100 and the target machine-mounted device 200 included in the distance data is below a predetermined threshold (step S42). In other words, the processor 33 determines whether the distance between the operator 2 and the machine 3 is below the predetermined threshold.

When determining that the distance between the operator device 100 and the machine-mounted device 200 is below the threshold (Yes in step S42), the processor 33 determines whether the operator 2 identified with the operator device 100 has an abnormal health condition (step S43). More specifically, the processor 33 determines whether the memory 31 stores a value indicating that the operator 2 has an abnormal health condition together with the operator ID of the operator device 100. This value is stored by the processor 33 in the memory 31 in step S34 in the preprocess shown in FIG. 11.

As shown in FIG. 12, when determining that the operator 2 has an abnormal health condition (Yes in step S43), the processor 33 reads the correction constant corresponding to the measurement value included in the health data of the operator 2 from the correction table (step S44).

More specifically, the processor 33 reads the correction constant corresponding to the measurement value of body temperature included in health data as shown in FIG. 4A from the correction table 360a based on body temperature shown in FIG. 6A, and stores the read correction constant for body temperature in the memory 31. The processor 33 reads the correction constant corresponding to the measurement value of blood pressure included in health data as shown in FIG. 4A from the correction table 360b based on blood pressure shown in FIG. 6B, and stores the read correction constant for blood pressure in the memory 31. The processor 33 reads the correction constant corresponding to the measurement value of heart rate included in the health data as shown in FIG. 4A from the correction table 360c based on heart rate shown in FIG. 6C, and stores the read correction constant for heart rate in the memory 31. The processor 33 then performs the processing in step S45.

As shown in FIG. 12, when the processor 33 determines that the operator 2 does not have an abnormal health condition, or in other words, has a normal health condition in step S43 (No in step S43), the processor 33 performs the processing in step S45 without performing the processing in step S44.

In step S45, the processor 33 reads the correction constant corresponding to the measurement value included in the posture data of the operator 2 from the corresponding correction table (step S45).

More specifically, the processor 33 reads the correction constant corresponding to the measurement value of acceleration included in posture data as shown in FIG. 4B from the correction table 360d based on acceleration shown in FIG. 7A, and stores the read correction constant for acceleration in the memory 31. The processor 33 reads the correction constant corresponding to the measurement value of the bent-over angle included in the posture data as shown in FIG. 4B from the correction table 360e based on the bent-over angle shown in FIG. 7B, and stores the read correction constant for the bent-over angle in the memory 31.

As shown in FIG. 12, the processor 33 then reads the correction constant corresponding to the attribute value included in attribute data from the corresponding correction table (step S46).

More specifically, the processor 33 reads the correction constant corresponding to the age included in the attribute data as shown in FIG. 4C from the correction table 360f based on the age shown in FIG. 8A, and stores the read correction constant for age in the memory 31. The processor 33 reads the correction constant corresponding to the value indicating the performance of the operator 2 included in the attribute data as shown in FIG. 4C from the correction table 360g based on the performance shown in FIG. 8B, and stores the read correction constant for performance in the memory 31.

As shown in FIG. 12, the processor 33 corrects the avoidability definition value (step S47).

More specifically, the processor 33 reads the avoidability definition value of the target machine 3 from the table in the risk definition value storage 350 shown in FIG. 5. The processor 33 calculates a corrected avoidability definition value with Formula (2) above. More specifically, the processor 33 adds the correction constants acquired in steps S44 to S46 to the read avoidability definition value. The processor 33 stores the calculated value as the corrected avoidability definition value in the memory 31.

When the processor 33 determines that the operator 2 does not have an abnormal health condition in step S43, the processing in step S44 is skipped. In this case, the processor 33 calculates the corrected avoidability definition value with Formula (3) above. More specifically, the processor 33 adds the correction constants read in steps S45 and S46 to the read avoidability definition value. The processor 33 stores the calculated value as the corrected avoidability definition value in the memory 31.

The processor 33 calculates the risk value with Formula (4) above (step S48). More specifically, the processor 33 calculates the sum of the corrected avoidability definition value acquired in step S47, and the definition value for hazardous event occurrence probability and the definition value for the frequency of accessing a hazard source stored in the risk definition value storage 350 shown in FIG. 5, and multiplies the calculated sum by the value of riskiness stored in the risk definition value storage 350 to acquire the risk value. The processor 33 stores the acquired risk value in the memory 31 together with the operator ID and the machine ID.

After the processor 33 calculates the risk values for the operators 2 adjacent to the machines 3 based on distance data received from each of the N machine-mounted devices 200 (Yes in step S41), the processor 33 transmits, to each operator device 100, a message including the risk value calculated in step S48 and an alert to the operator 2 corresponding to the risk value (step S49).

For example, when the risk value calculated in step S48 exceeds a threshold, the processor 33 transmits, to the operator device 100 worn by the corresponding operator 2, information that enables identification of the machine 3 identified with the machine ID and a warning message based on the risk value. For example, the processor 33 outputs a warning message stating "The risk value from a lathe (ID: 0002) has exceeded a first threshold. The risk is on the level 4. Keep away from the lathe (ID: 0002)".

In another example, the processor 33 may output a warning message in the manner described below. When the risk value calculated in step S48 exceeds a threshold, the processor 33 transmits, to the operator device 100 worn by the operator 2 adjacent to the machine 3, information identifying the machine 3 identified with the machine ID and a warning message based on the risk value. The processor 33 transmits the warning message to the operator 2 determined as having the risk value exceeding the threshold and other operators 2 adjacent to the machine 3 with the risk values not exceeding the threshold.

For example, the processor 33 outputs a warning message stating "The next warning message is for the operator ID 1001. The risk value from the lathe (ID: 0002) has exceeded the first threshold. The risk is on the level 4. Keep away from the lathe (ID: 0002). This is the warning message for the operator ID 1001".

Outputting a warning message not only to the operator 2 with the risk value exceeding the threshold but also to other operators adjacent to the machine 3 has the advantages described below. For example, although the operator 2 with the operator ID 1001 ignores the warning message, other operators 2 can urge the operator 2 with the operator ID 1001 to escape. When the physical conditions of the operator 2 with the operator ID 1001 suddenly change and the operator 2 cannot deal with the situation, other operators 2 can rescue the operator 2 with the operator ID 1001 or request a rescue to, for example, a manager or other operators.

As described above, the structure according to the embodiment corrects, among the three factors of hazard occurrence probability used for calculating a risk value, the avoidability definition value indicating the possibility of the operator 2 avoiding a hazard in accordance with the physical conditions and the attributes of the operator 2. In other words, the avoidability definition value is calculated for each operator 2, and the risk value is calculated using the calculated avoidability definition value. This structure enables calculation of a risk value based on the physical conditions of each operator 2 when the operator 2 and the machine 3 are spaced apart from each other.

Modification 1

Figure 13:
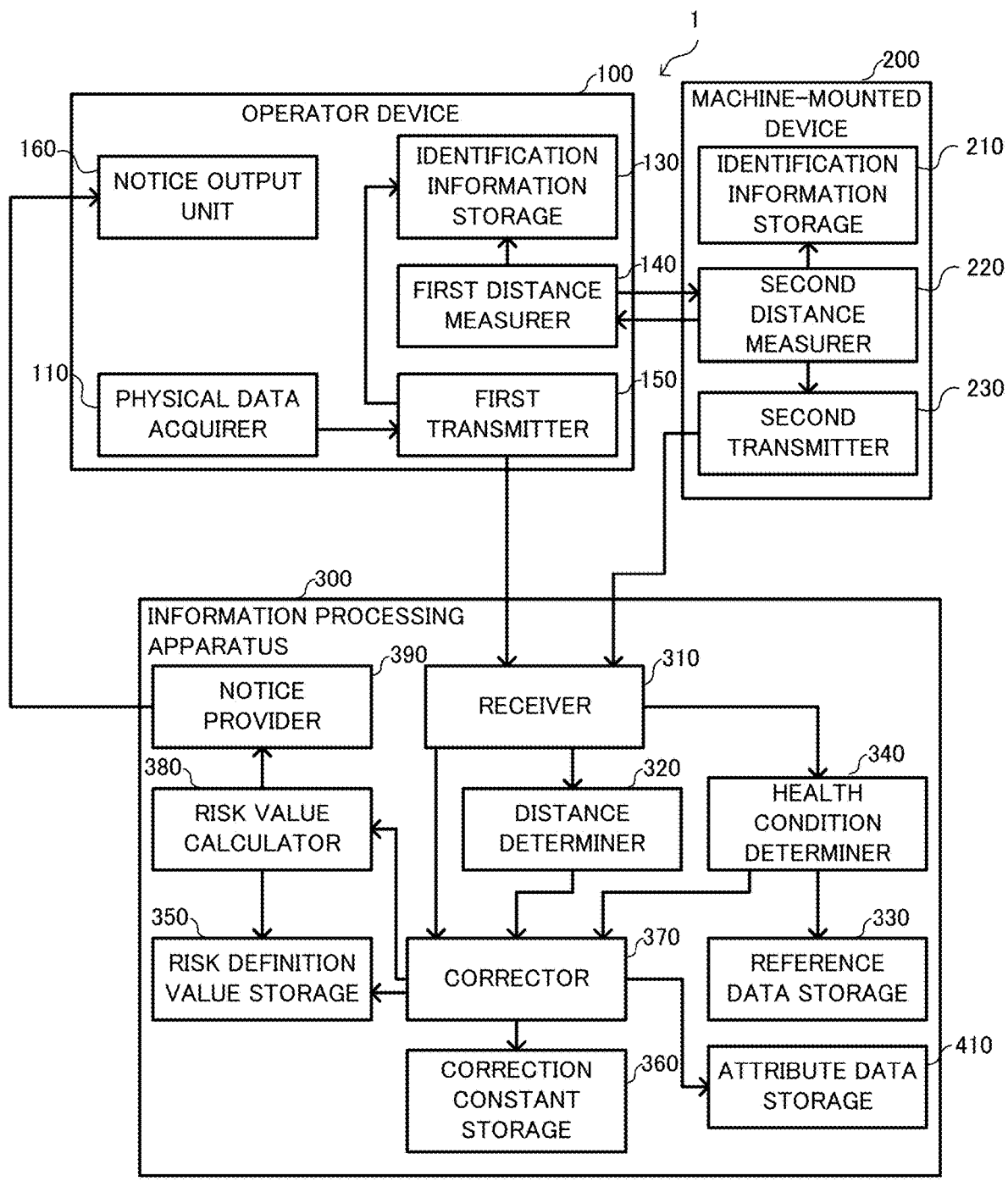
FIG. 13 is a functional block diagram of a risk value calculation system according to Modification 1.

As shown in FIG. 1, in the above embodiment, each operator device 100 includes the attribute data storage 120 that stores attribute data indicating the attributes of the operator 2. The embodiment is not limited to this structure. As shown in FIG. 13, the operator device 100 may eliminate the attribute data storage 120, and the information processing apparatus 300 may include an attribute data storage 410 that stores the attribute data indicating the attributes of the operator 2. In this case, the first transmitter 150 may transmit health data and posture data to the information processing apparatus 300. The corrector 370 may acquire attribute data from the attribute data storage 410 to correct the avoidability definition value.

Modification 2

Figure 14:
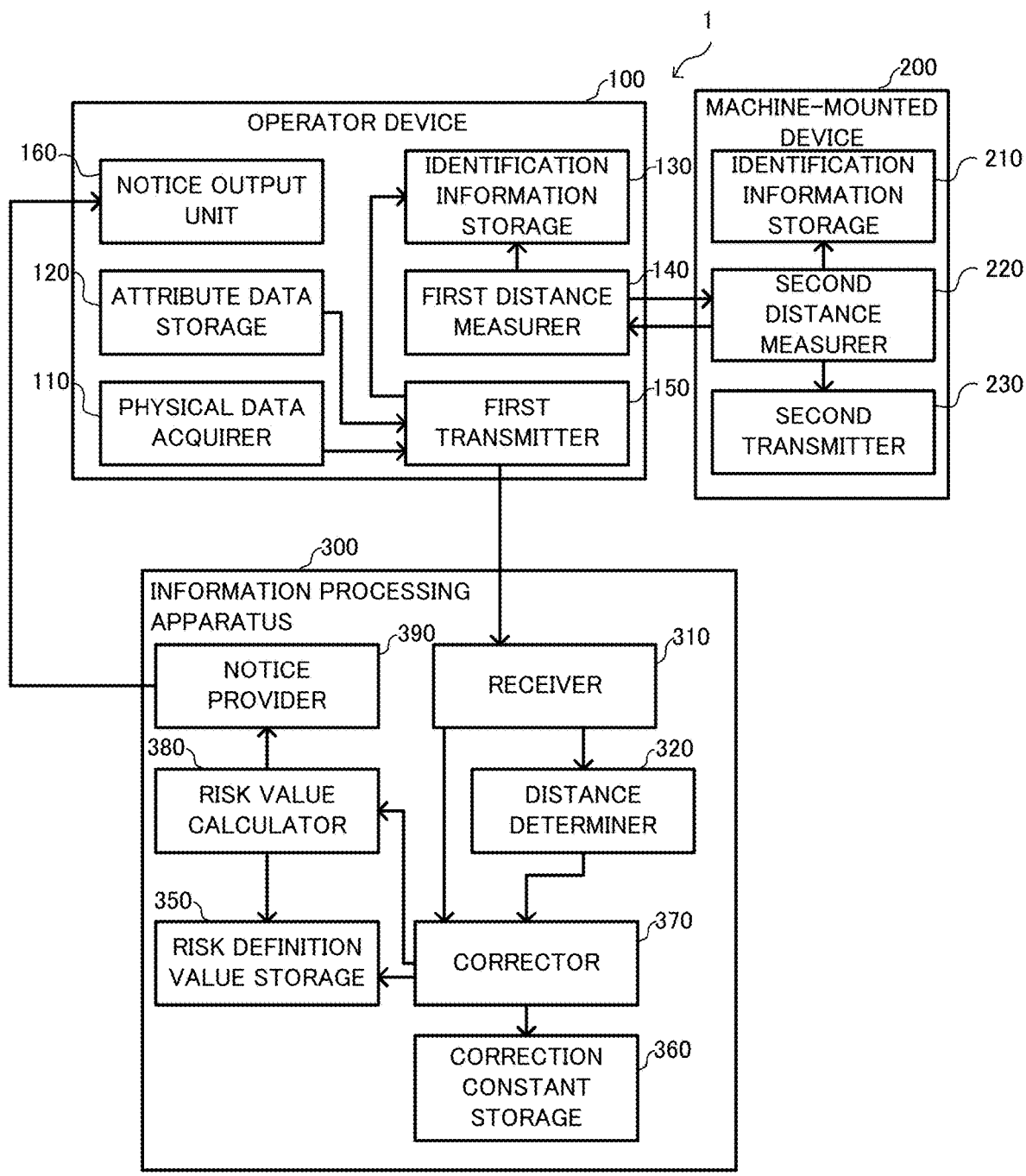
FIG. 14 is a functional block diagram of a risk value calculation system according to Modification 2.

In the embodiment, the health condition determiner 340 determines whether each operator 2 has an abnormal health condition based on health data. The embodiment is not limited to this structure. As shown in FIG. 14, the information processing apparatus 300 may eliminate the health condition determiner 340 and the reference data storage 330. In this case, the corrector 370 may use Formula (2) above each time to calculate the corrected avoidability definition value.

Modification 3

In the embodiment, the corrector 370 corrects the avoidability definition value in accordance with the attribute value of the operator 2 indicated by the attribute data. In some embodiments, the corrector 370 may correct the avoidability definition value based simply on the healthcare measurement value and the posture measurement value without reflecting the attribute value.

Modification 4

In the embodiment, the second distance measurer 220 shown in FIG. 1 transmits the distance measurement signal to each operator device 100, and calculates the distance between the operator device 100 and the machine-mounted device 200 based on the electric field intensity of the response signal received from the operator device 100. The embodiment is not limited to this structure. The first distance measurer 140 may transmit the distance measurement signal including the operator ID to the machine-mounted device 200. In this case, the second distance measurer 220 transmits the response signal including the machine ID to the operator device 100. The first distance measurer 140 may calculate the distance to the machine-mounted device 200 based on the electric field intensity of the received response signal.

Modification 5

In the embodiment, the distance between the operator device 100 and the machine-mounted device 200 is measured based on the electric field intensity of the received response signal. The embodiment is not limited to this structure. For example, the first distance measurer 140 and the second distance measurer 220 each may include a timing device. One of the measurers that transmits a response signal includes time information indicating transmission time in the response signal. The other measurer that receives the response signal may calculate radio propagation time based on the time at which the response signal is received and transmission time information included in the information indicated by the response signal, and may calculate the distance between the operator device 100 and the machine-mounted device 200 based on the radio propagation time.

In the embodiment, the physical data acquirer 110 in each operator device 100 acquires the health data and posture data of the operator 2. In some embodiments, the physical data acquirer 110 may acquire either health data or posture data.

In the embodiment, to calculate the corrected avoidability definition value, the corrector 370 adds, to the avoidability definition value stored in the risk definition value storage 350, the correction constants based on body temperature, blood pressure, and heart rate, the correction constants based on acceleration and bent-over angle, and the correction constants based on age and performance as in Formula (2). The embodiment is not limited to this structure. The corrector 370 may add a value acquired by multiplying these correction constants together to the avoidability definition value stored in the risk definition value storage 350. In some embodiments, the corrector 370 may multiply the avoidability definition value stored in the risk definition value storage 350 by the value acquired by multiplying these correction constants together.

The corrector 370 may not use all the correction constants to calculate the corrected avoidability definition value. The corrector 370 may weight one or more correction constants or all the correction constants.

In the embodiment, in determining whether the operator has an abnormal health condition, the information processing apparatus 300 calculates the standard deviations of the measurement values included in health data to determine whether any of the standard deviations exceeds a threshold. The embodiment is not limited to this structure. For example, tolerance data defining the upper limit and the lower limit of the tolerances of the measurement values of body temperature, blood pressure, and heart rate for the operator 2 having a normal health condition may be prestored in the memory 31. The information processing apparatus 300 may determine whether the measurement values included in the health data of the operator 2 deviate from the tolerances based on the measurement values and tolerance data. In this case, the information processing apparatus 300 determines that the operator 2 has an abnormal health condition when the measurement values deviate from the tolerances. The tolerances may be defined for each operator 2.

In the embodiment, the health data of the operator 2 includes the measurement values of the body temperature, blood pressure, and heart rate of the operator 2. However, the embodiment is not limited to this structure.

For example, the operator device 100 may detect coughing of the operator 2. In this case, the sensor 11 may include a microphone and an acceleration sensor to serve as a cough detection sensor. The cough detection sensor may detect whether the operator 2 is coughing and the level of a cough based on the sound collected by the microphone and vibrations of the body of the operator 2 detected by the acceleration sensor. The information processing apparatus 300 can determine whether the operator 2 is in good health based on data indicating the level of a cough of the operator 2 received from the operator device 100. For example, the information processing apparatus 300 may determine that the operator 2 is in poor health condition when the operator 2 keeps coughing intensely.

The operator device 100 may detect sweating of the operator 2. In this case, the sensor 11 may include a sensor for detecting sweating and a temperature sensor for measuring the temperature inside a factory. The operator device 100 transmits data indicating sweating of the operator 2 and data indicating the temperature inside the factory to the information processing apparatus 300. The information processing apparatus 300 can determine whether the operator 2 is in good health based on the sweating level of the operator 2 and the temperature inside the factory. For example, when the operator 2 is sweating excessively although the temperature inside the factory is not high, the information processing apparatus 300 may determine that the operator 2 is in poor health condition.

In the embodiment, the information processing apparatus 300 corrects the avoidability definition value, serving as a risk factor parameter, and calculates the risk value with the corrected avoidability definition value. In some embodiments, the information processing apparatus that corrects the avoidability definition value may be different from the information processing apparatus that calculates the risk value. For example, the information processing apparatus 300 may correct the avoidability definition value, and provide the corrected avoidability definition value to another information processing apparatus. The other information processing apparatus may calculate the risk value with the corrected avoidability definition value provided.

In some embodiments, the information processing apparatus 300 may correct the avoidability definition value in accordance with the physical conditions of the operator 2, and provide the corrected avoidability definition value to the operator device 100 worn by the operator 2. In this case, the operator device 100 may calculate the risk value with the corrected avoidability definition value provided. In some embodiments, the information processing apparatus 300 may correct the avoidability definition value in accordance with the physical conditions of the operator 2, and provide the corrected avoidability definition value to the machine-mounted device 200 for which the distance to the operator 2 has been acquired. In this case, the machine-mounted device 200 calculates the risk value of the operator 2 adjacent to the machine-mounted device 200 with the corrected avoidability definition value provided.

A recording medium for recording the above program may be a non-transitory computer-readable recording medium, such as a magnetic disk, an optical disc, a magneto-optical disc, a flash memory, a semiconductor memory, or a magnetic tape.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

REFERENCE SIGNS LIST

1 Risk value calculation system
2 Operator
3 Machine
4 PLC
11, 23 Sensor
12, 21, 31 Memory
13, 22, 32 Communication interface
14 Output device
15, 24, 33 Processor
19, 29, 39 Bus
100 Operator device
110 Physical data acquirer
111 Medical sensor
112 Posture sensor 120 Attribute data storage
121, 211 Measurement program
130, 210 Identification information storage
131, 221, 321 Antenna
140 First distance measurer
150 First transmitter
160 Notice output unit
200 Machine-mounted device
220 Second distance measurer
230 Second transmitter
231 Electric field intensity sensor
300 Information processing apparatus
310 Receiver
311 Risk value calculation program
320 Distance determiner
330 Reference data storage
340 Health condition determiner
350 Risk definition value storage
360 Correction constant storage
360a, 360b, 360c, 360d, 360e, 360f, 360g Correction table
370 Corrector
380 Risk value calculator
390 Notice provider

The invention claimed is:

1. A risk value calculation system, comprising:
an operator device wearable by an operator; and
an information processing apparatus to calculate a risk value indicating a level of risk,
wherein the operator device includes a physical data acquirer to acquire at least one of health data indicating a health condition of the operator or posture data indicating a posture of the operator, and
the information processing apparatus includes
a distance determiner to determine whether a distance between the operator and a machine is below a predetermined threshold,
a corrector to correct, in response to the distance determiner determining that the distance is below the predetermined threshold, an avoidability definition value defined as a value indicating a possibility of the operator avoiding a hazard caused by the machine in accordance with at least one of the health condition of the operator indicated by the health data acquired from the operator device or the posture of the operator indicated by the posture data acquired from the operator device, and
a risk value calculator to calculate the risk value by substituting the avoidability definition value corrected by the corrector and a riskiness definition value defined as a value indicating a degree of a hazard caused by the machine into a calculation function indicating a relationship between the avoidability definition value, the riskiness definition value, and the risk value.

2. The risk value calculation system according to claim 1, wherein
the health data includes a healthcare measurement value acquired by measuring at least one health factor indicating the health condition,
the posture data includes a posture measurement value acquired by measuring at least one posture factor indicating the posture, and
the corrector calculates the corrected avoidability definition value by substituting the avoidability definition value before being corrected and at least one of a first correction constant corresponding to the healthcare measurement value or a second correction constant corresponding to the posture measurement value into a correction function indicating a relationship between the healthcare measurement value, the posture measurement value, the avoidability definition value before being corrected, and the corrected avoidability definition value.

3. The risk value calculation system according to claim 2, wherein
the corrector corrects, in response to the distance determiner determining that the distance is below the predetermined threshold, the avoidability definition value in accordance with an attribute of the operator and at least one of the health condition or the posture.

4. The risk value calculation system according to claim 3, wherein
the correction function indicates a relationship between the healthcare measurement value, the posture measurement value, an attribute value indicating the attribute, the avoidability definition value before being corrected, and the corrected avoidability definition value, and
the corrector calculates the corrected avoidability definition value by substituting, into the correction function, a third correction constant corresponding to the attribute, the avoidability definition value before being corrected, and at least one of the first correction constant corresponding to the healthcare measurement value or the second correction constant corresponding to the posture measurement value.

5. The risk value calculation system according to claim 4, wherein
the information processing apparatus further includes
a risk definition value storage to store the avoidability definition value for the machine and the riskiness definition value for the machine, and
a correction constant storage to store the first correction constant corresponding to the healthcare measurement value, the second correction constant corresponding to the posture measurement value, and the third correction constant corresponding to the attribute value indicating the attribute.

6. The risk value calculation system according to claim 4, wherein
the information processing apparatus further includes a health condition determiner to determine whether the operator is in good health based on the health data, and
the corrector corrects, in response to the health condition determiner determining that the operator is in good health, the avoidability definition value in accordance with the posture, and corrects, in response to the health condition determiner determining that the operator is in poor health, the avoidability definition value in accordance with the health condition and the posture or in accordance with the health condition.

7. The risk value calculation system according to claim 4, wherein
the operator device further includes
an attribute data storage to store attribute data including the attribute value, and
a first communicator to communicate with the information processing apparatus, and
the first communicator transmits the health data, the posture data, and the attribute data to the information processing apparatus.

8. The risk value calculation system according to claim 4, wherein the information processing apparatus further includes an attribute data storage to store attribute data including the attribute value, the operator device further includes a first communicator to communicate with the information processing apparatus, and the first communicator transmits the health data and the posture data to the information processing apparatus.

9. The risk value calculation system according to claim 1, further comprising:

a machine-mounted device mountable on the machine, wherein the operator device further includes a first distance measurer to communicate with the machine-mounted device to measure a distance between the operator device and the machine-mounted device, and the machine-mounted device includes a second distance measurer to communicate with the operator device to measure the distance, and a second communicator for transmitting information indicating the distance to the information processing apparatus.

10. The risk value calculation system according to claim 1, further comprising:

a machine-mounted device mountable on the machine, wherein the machine-mounted device includes a second distance measurer to communicate with the operator device to measure a distance between the operator device and the machine-mounted device, and the operator device further includes a first distance measurer to communicate with the machine-mounted device to measure the distance, and a first communicator to transmit information indicating the distance to the information processing apparatus.

11. An information processing apparatus, comprising:

a communicator to communicate with an operator device wearable by an operator and a machine-mounted device mountable on a machine;

a distance determiner to determine whether a distance between the operator device and the machine-mounted device acquired from the operator device or the machine-mounted device is below a predetermined threshold;

a corrector to correct, in response to the distance determiner determining that the distance is below the predetermined threshold, an avoidability definition value defined as a value indicating a possibility of the operator avoiding a hazard caused by the machine in accordance with at least one of a health condition of the operator indicated by health data acquired from the operator device or a posture of the operator indicated by posture data acquired from the operator device; and a risk value calculator to calculate a risk value indicating a level of risk by substituting the avoidability definition value corrected by the corrector and a riskiness definition value defined as a value indicating a degree of a hazard caused by the machine into a calculation function indicating a relationship between the avoidability definition value, the riskiness definition value, and the risk value.

12. A non-transitory computer readable recording medium storing a program for causing a computer to perform operations comprising:

acquiring at least one of health data indicating a health condition of an operator or posture data indicating a posture of the operator from an operator device wearable by the operator;

determining whether a distance between the operator device and a machine-mounted device mountable on a machine is below a predetermined threshold;

correcting, in response to the distance being below the threshold, an avoidability definition value defined as a value indicating a possibility of the operator avoiding a hazard caused by the machine in accordance with at least one of the health condition of the operator indicated by the health data or the posture of the operator indicated by the posture data; and calculating a risk value indicating a level of risk by substituting the corrected avoidability definition value and a riskiness definition value defined as a value indicating a degree of a hazard caused by the machine into a calculation function indicating a relationship between the avoidability definition value, the riskiness definition value, and the risk value.

* * * * *